United States Patent [19]

Horecker

[11] 4,374,197

[45] Feb. 15, 1983

[54] PROCESS FOR THYMOSIN $\alpha_1$

[75] Inventor: Bernard L. Horecker, New York, N.Y.

[73] Assignee: Hoffmann-La Rocche Inc., Nutley, N.J.

[21] Appl. No.: 300,324

[22] Filed: Sep. 8, 1981

Related U.S. Application Data

[63] Continuation-in-part of Ser. No. 201,687, Oct. 30, 1980, abandoned.

[51] Int. Cl.³ .......................... C12P 21/00; C12N 9/10
[52] U.S. Cl. ........................................ 435/68; 435/193
[58] Field of Search .................................. 435/68, 193

[56] References Cited

U.S. PATENT DOCUMENTS 4,293,455 10/1981 Merrifield et al. ...................... 260/8

FOREIGN PATENT DOCUMENTS 52-41294 3/1977 Japan .................................. 435/193

OTHER PUBLICATIONS

Palmeter, R. D. et al., Proc. Natl. Aca. Sci. 75, 9498, (1928).
Granger et al., Proc. Nat. Acad. Sci. 73, 3010–3014, (1976).
Wong et al., Biochemistry, vol. 19, pp. 3233–3238, (1980).
Bloemendal, Science, vol. 197, pp. 127–138, (1977).
Woodford et al., The Journal of Biological Chemistry, vol. 254, No. 12, pp. 4993–4999, (1979).

*Primary Examiner*—Lionel M. Shapiro
*Attorney, Agent, or Firm*—Jon S. Saxe; George M. Gould; John B. Wilson

[57] ABSTRACT

A process is described for the preparation of thymosin $\alpha_1$ from desacetylthymosin $\alpha_1$ in the presence of an acetylating agent and a biologically active ribosome preparation. Thymosin $\alpha_1$ is useful in increasing T-cell numbers and normalizing immune function in patients with thymic dependent primary immunodeficiency diseases and in cancer patients who are immunodepressed.

10 Claims, No Drawings

PROCESS FOR THYMOSIN $\alpha_1$

This application is a continuation-in-part of U.S. patent application Ser. No. 201,687, filed Oct. 30, 1980, now abandoned.

BACKGROUND OF THE INVENTION

Thymosin $\alpha_1$ occurs naturally and its isolation and biological activity has been described in U.S. Pat. No. 4,079,127. Thymosin $\alpha_1$ is a biologically active peptide hormone isolated from thymosin fraction 5 and has its amino-terminus acetylated. The preparation of desacetyl thymosin $\alpha_1$ by solid state synthesis is described by Wong and Merrifield, Biochemistry 19, 3233–3239 (1980), and, therefore, is available as a starting material in producing thymosin $\alpha_1$.

In U.S. patent application Ser. No. 137,939, filed Apr. 7, 1980, now U.S. Pat. No. 4,293,455 for $N^\alpha$-DESACETYL THYMOSIN $\alpha_1$ AND PROCESS [inventors: Merrifield and Wong], there is disclosed the conversion of [Lys (Tfa)$^{14,17,19,20}$]-desacetyl thymosin $\alpha_1$, produced by solid state synthesis, into thymosin $\alpha_1$ by acetylation with pyridine-acetic anhydride, followed by removal of the trifluroacetate (Tfa) protecting group with aqueous pyridine.

Bloemendal, H. Science 197, 127–138 (1977) has reported that both enzymes and structural proteins may be acetylated by other proteins at the amino-terminus, with acetylation taking place on the nascent protein chain containing 25 or more amino acid residues during biosynthesis of the chain [Palmiter, R.D., et al., Proc. Nat. Acad Sci 75 9498 (1978)]. An enzyme present in extracts from calf lens will acetylate synthetic desacetyl $\alpha$-melanocyte stimulating hormone [Granger, et al. Proc. Nat. Acad. Sci 73, 3010–3014 (1976)]. A pituitary enzyme preparation will transfer acetyl groups from acetyl-Coenzyme A to ACTH and ACTH fragments [Woodford and Dixon, J. Biol. Chem. 254, 4993–4999 (1979)]

DETAILED DESCRIPTION OF THE INVENTION

The present invention relates to the amino-terminal acetylation of a completed chain of an hormonal protein by preparations having transacetylase activity. In particular the present invention relates to the selected amino terminus acetylation of desacetyl thymosin $\alpha_1$ to thymosin $\alpha_1$ using ribosome preparations which contain transacetylase activity.

For the process of the present invention it is possible to use any biologically active ribosome preparation prepared by art recognized procedures from either animal or plant sources. A biologically active ribosome preparation contains transacetylase activity. In particular the sources for the ribosome preparation include any animal tissue examples of which are thymus gland, liver, reticulocytes, pituitary gland, muscle, heart, kidney, brain, skin, and the like; and includes plant cells examples of which are wheat germ. Especially preferred sources of ribosome preparations are the thymus gland and wheat germ. The cellular constituency of wheat germ or of tissue from the thymus gland may be disrupted by any art recognized means which permit obtaining extracts containing biologically active ribosomes. It is preferred that the ribosome preparations for the present process be prepared freshly each day in which the process is carried out, in order to avoid decrease or loss of transacetylase activity therein upon storage.

The method of Paterson as disclosed in Proc. Nat. Acad. Sci. 70, 2330–2334 (1973) is especially useful in preparing the S30 fraction containing ribosome from wheat germ. The method of Shockelford as disclosed in J. Biol. Chem. 254, 4220–4226 (1949) is especially suitable in ribosome preparation from the thymus gland.

Generally the ribosome preparation is conveniently prepared from cellular material obtained from wheat germ or tissue of thymus gland by homogenization of the cellular material in a suitable buffer such as tris(hydroxymethyl)aminomethane hydrochloride (Tris-HCl), phosphate, N-2-hydroxyethyl piperazine-N-2-ethane sulfonic acid (HEPES), or the like, permitting a pH of about 6.5 to 7.5, the preferred pH being 7.5 and the buffer preferably containing $MgCl_2$ from about 2 to 5 mM, preferably 3 mM, and dithiothreitol (DTT) from about 0.5 to 10 mM, preferably 1 mM. The homogenized material is centrifuged at low temperatures and the supernatant removed without the surface layer of fat. The designated S30 fraction derived by centrifugation is passed through a gel filtration column such as Sephadex G-25 (coarse), with collection of the turbid fractions. These fractions are pooled, centrifuged at about 180,000 xg and the precipitate containing ribosome is obtained. This precipitate may be used or may be further purified by art recognized methods so as to isolate therefrom the transacetylase. In the process of the invention the precipitate is used after dissolving it in a solvent which is an aqueous buffer of Tris-HCl at pH 7.5 containing DTT in an amount described above and KCl from about 0.5 to 3.0 M, preferably 1.5 M. The solvent may also contain $MgCl_2$ in an amount described above. The resulting solution constitutes a buffered solution of the ribosome preparation. The presence of KCl has surprisingly been found to enhance specific $NH_2$-terminal acetylation of desacetyl thymosin $\alpha_1$.

The acetylating agent useful in the present process is any suitably activated acetate compound which may be acceptable to the transacetylase activity of the ribosome preparation in carrying out the invention process. Among such acetylating agents (activated acetate compounds) there are included N-acetylthioethanolamine and acetyl Coenzyme A. The preferred activated acetate compound is acetyl Coenzyme A (acetyl CoA). The acetyl CoA may be tritiated acetyl CoA ($^3$H-acetyl CoA) which can be used both for acetylation and as a marker in purification and identification of the final product of the invention.

$N^\alpha$-desacetyl thymosin $\alpha_1$ may be prepared and obtained by the method disclosed by Wong and Merrifield [Biochemistry 19, 3233–3238 (1980)]. $N^\alpha$-desacetyl thymosin acts as substrate receiving the acetyl group from acetyl coenzyme A in the presence of the ribosome preparation to produce thymosin $\alpha_a$ as final product. While there are a number of possible sites for acetylation on the desacetyl thymosin $\alpha_1$ molecule, it has been found unexpectedly that the present process selectively acetylates the terminal amino group to provide thymosin $\alpha_1$.

The overall invention process relates to preparing thymosin $\alpha_1$ by reacting $N^\alpha$-desacetylthymosin $\alpha_1$ with an acetylating agent in the presence of a biologically active ribosome preparation. More particularly the present process typically comprises in combination the following steps:

(a) Lyophilizing an aqueous solution containing acetyl CoA as the acetylating agent and desacetyl thymosin $\alpha_1$ as the substrate in a micro-polypropylene test tube. The amount of substrate and acetylating agent used is not critical. A suitable concentration range of substrate is from about 1 μM to about 200 μM, with the preferred amount being 80 μM. A suitable concentration range of acetylating agent is from about 1 μM to about 500 μM, with the preferred amount being 400 μM.

(b) Initiating the reaction by adding a buffered solution of the ribosome preparation, the amount added not being critical. The preferred amount of ribosome preparation added is about 13 μg of ribosome per 10 μl of reaction mixture.

(c) Incubating the reaction mixture for a sufficient time and at a suitable temperature permitting acetylation of the substrate. A preferred temperature range for the reaction is about 30° C. to about 37° C., most preferably about 35° C. Under these conditions the reaction is generally completed in about 20 minutes.

(d) Adding an alkaline solution such as NaOH to a final concentration sufficient to destroy any excess acetyl Co A but insufficient to significantly interfere with the integrity of the final product. The preferred final concentration of NaOH is about 1N, with incubation thereafter at about 35° for about 15 minutes. Then the reaction mixture is neutralized using a concentrated mineral acid such as HCl. Alternatively a solution of 10% trichloroacetic acid may be used to precipitate protein.

(e) Obtaining the final product from the reaction mixture by any art recognized isolation procedure. The preferred procedure for isolation of the final product is by chromatographic procedures. A particularly preferred chromatographic procedure is high performance reversed phase liquid chromatography as described by Rubinstein, Anal. Biochem. 98, 1–7 (1979).

In the combination of reaction steps, i.e. steps a–e above, it has been found to be advantageous for purposes of facilitating isolation and identification of final product to add thymosin $\alpha_1$ as a carrier. This addition of thymosin $\alpha_1$ as a carrier can be made at any time during the overall reaction process, with the amount of added thymosin $\alpha_1$ not being critical to the formation of reaction product. It is preferred that addition of thymosin $\alpha_1$ as a carrier be made subsequent to a reaction between substrate, acetylating agent and the transacetylase, preferably after 10–30 minutes from the start of such reaction and preferably in an amount of from about 1–50 nmol, especially about 24 nmol.

The following Examples further illustrate the invention but are not meant to limit the invention in scope or spirit.

EXAMPLE 1

Preparation of Wheat-Germ Extracts

The 30,000 xg supernatant (S30) of wheat germ was prepared by modifications of the procedure of Roberts and Paterson. Proc. Nat. Acad. Sci. 70, 23302334 (1973). Wheat germ (6 g) was ground for 1 minute in a chilled mortar with an equal weight of sand and 20 ml of a Tris-HCl buffer solution containing 50 mM Tris-HCl, pH 7.5, 3 mMg Cl$_2$, and 1 mM DTT. The homogenate was centrifuged at 30,000 xg for 20 minutes at 0–2° C., and the supernatant was removed, without the surface layer of fat. The S30 fraction was passed through a column (60×2 cm) of Sephadex G-25 (coarse), equilibrated with 50 mM Tris-HCl, pH 7.5, containing 1 mM DTT, at a flow rate of 1.4 ml/min. The turbid fractions were pooled and centrifuged at 180,000 xg for 2 hours at 2° C. The precipitate was suspended in 0.75 ml of 50 mM Tris HCl buffer, pH 7.5, containing 3 mM MgCl$_2$, 1 mM DTT and 1.5 MKCl to provide the wheat germ ribosome preparation.

EXAMPLE 2

Acetylation of Desacetyl Thymosin $\alpha_1$ with Wheat Germ Ribosome Preparation Solutions containing [$^3$H] acetyl CoA (2.1 nmol) and desacetyl thymosin $\alpha_1$ (400 pmol) were lyophilized in a micro-polypropylene test tubes. The reactions were started by addition of 10 μl of the wheat germ ribosome preparation of Example 1. After incubation at 35° C. for 20 minutes, 40 μl of an aqueous solution containing 80 μg (24 nmol) of thymosin $\alpha_1$ was added as carrier. This was followed by NaOH to a final concentration of 1 N and incubation at 35° C. for 15 minutes to destroy excess acetyl CoA. The solution was then neutralized with concentration HCl.

EXAMPLE 3

High Performance Reversed Phase Liquid Chromatography (HPLC)

High performance liquid chromatography (HPLC) was carried out on a reverse-phase column (Ultrasphere-octyl, 4.6×250 mm, Altex Scientific, Inc. as described by Rubinstein, Anal. Biochem. 98, 17 (1979)). The column was eluted with a 2-hour linear gradient of 0–40% (vol/vol)1-propanol in 1 M formic acid/0.2 M pyridine (pH 2.8) at a flow rate of 0.33 ml per minute and fractions were collected every 2.5 minutes. At 20 second intervals 5 μl samples were diverted to a fluorescence-detection system. Aliquots were also counted for radioactivity.

Transfer of Acetyl Groups to Desacetyl Thymosin $\alpha_1$ Catalyzed by a Ribosomal Fraction from Wheat Germ After incubation of [$^3$H]acetyl CoA (2.1 nmol) desacetyl thymosin $\alpha_1$ (400 pmol) in the presence of a ribosomal fraction from wheat germ analysis by HPLC revealed the presence of a radioactive peak that co-eluted with the thymosin $\alpha_1$ carrier. This peak was not formed in a control reaction mixture from which desacetyl thymosin $\alpha_1$ had been omitted or in which thymosin $\alpha_1$ replaced desacetyl thymosin $\alpha_1$ as substrate. In the last experiment radioactivity was recovered only in the peaks corresponding to acetic acid and acetyl CoA; there was thus no evidence for acetylation of $\epsilon$-NH$_2$-lysyl groups under the conditions employed in these experiments. Some acetylation of ribosomal proteins was also observed but this was small compared to that of desacetyl thymosin $\alpha_1$.

Characterization of the Labeled Product Formed for Desacetyl Thymosin $\alpha_a$ In order to confirm the identification of the labeled product as thymosin $\alpha_1$, the radioactive fractions corresponding to the thymosin $\alpha_1$ peak were pooled and rechromatographed under the same conditions, but with a shallower gradient (4 instead of 2 hours). The radioactive peak corresponding to thymosin $\alpha_1$ was collected and digested with trypsin. Radioactivity was recovered only in the fractions containing the NH$_2$-terminal tryptic peptide, AcSer-Asp-Ala-Ala-Val-Asp- Thr-Ser-Ser-Glu-Ile-Thr-Thr-Lys, which emerged slightly ahead of the position where thymosin $\alpha_1$ would be eluted. The identity of this peptide was confirmed by amino acid analysis. The absence of radioactivity elsewhere supports the earlier conclusion that no acetylation of $\epsilon$-NH$_2$-groups of lysine occurred.

Extent of Conversion

From the amino acid analysis it was calculated that the recovery of the NH$_2$-terminal tryptic peptide was 2.3 nmol, or 9.6% based on the carrier thymosin $\alpha_1$ added to the reaction mixture (23.9 nmol). From the radioactivity, corrected for the recovery of NH$_2$-terminal peptide, and the specific activity of the acetyl CoA, we calculated that 59.6 pmol of radioactive thymosin $\alpha_1$ had been formed. This represents a conversion of 15% of the 400 pmol of desacetyl thymosin $\alpha_1$ present in the original reaction mixture.

Conditions of NH$_2$-terminal Acetylation

High concentrations of KCl, approximately 1.5 M enhanced NH$_2$-terminal acetylation. The optimum pH was below 7.5; above this pH the extent of NH$_2$-terminal acetylation was greatly decreased. Below pH 6.5 a mixture of radioactive products was formed from added desacetyl thymosin $\alpha_1$ that eluted later than desacetyl thymosin $\alpha_1$ or thymosin $\alpha_1$ from the Ultraphereoctyl column employed for reversed phase HPLC. The addition of KCl also reduced this non-specific acetylation.

EXAMPLE 4

Preparation of Thymus Gland Extracts

Thymus glands (12 g) from two freshly killed calfs were homogenized in a Dounce homogenizer with 2 volumes of 20 mM Tris-HCl, containing 3 mM MgCl$_2$, 25 mM NaCl, 1 mM DTT and 250 mM sucrose, pH 7.5. The homogenate was centrifuged at 12,000 xg for 10 minutes and the supernatant fractions were centrifuged at 30,000 xg for 10 minutes. The S30 fraction was passed through a column (60×2 cm) of Sephadex G-25 (coarse), previously equilibrated with 50 mM Tris-HCl, pH 7.5, containing 1 mM DTT and 3 mM MgCl$_2$, at a flow rate of 1.4 ml/min. The turbid fractions representing the excluded volume of the column were the source of the acetylating (transacetylase) enzyme. All operations were carried out at 0°–2° C. The yield may be significantly increased by carrying out the acetylation with the ribosomes suspended in Tris-HCl buffer containing 3 mM MgCl$_2$ and 1 mM DTT, and with the addition of 1.5 MKCl as described in Example 2.

EXAMPLE 5

Acetylation of desacetylthymosin $\alpha_1$ with S30 Preparation from Thymus Gland Solutions containing [3H] acetyl CoA (1.05 nmol) with or without desacetyl thymosin $\alpha_1$ (204 pmol) were lyophilized in micropolypropylene test tubes. The reactions were started by addition of 5 $\mu$l of the thymus S30 fraction (4.1 $\mu$g). After incubation at 35° C. for 20 minutes, the reaction was stopped by the addition of 2 ml of 10% CCL$_3$COOH. The precipitate was collected on Millipore (HA, 0.45 $\mu$m) filters. The filters were washed with 5% CCl$_3$COOH, dried, and assayed for radioactivity in 10 ml of Aquasol.

| | | |
|---|---|---|
| cpm in the sample with desacetylthymosin $\alpha_1$ | = | 1455 |
| cpm in the sample without desacetylthymosin $\alpha_1$ | = | 602 |
| Net cpm | = | 858 |
| specific activity of [3H] acetyl CoA | = | 1429 cpm/pmol |
| acetylated 0.6 pmol | = | 0.3% |

Alternatively the fractions from the Sephadex G-25 column may be centrifuged at 180,000 xg for 2 hours at 2° C. and the precipitated ribosomes suspended in the Tris-HCl buffer mixture as described in Example 1.

I claim:

1. A process for preparing thymosin $\alpha_1$ comprising reacting N$^\alpha$-desacetylthymosin $\alpha_1$ with an acetylating agent in the presence of transacetylase in an aqueous solvent, so as to selectively acetylate the N$^\alpha$-amino group of N$^\alpha$-desacetylthymosin $\alpha_1$.

2. A process according to claim 1 wherein the acetylating agent is acetyl-Coenzyme A.

3. A process according to claim 1 wherein said transacetylase is provided as a biologically active ribosome preparation.

4. A process according to claim 3 wherein the ribosome preparation is prepared from animal tissue.

5. A process according to claim 4 wherein the animal tissue is selected from a group consisting of thymus gland, liver, reticulocytes, pituitary gland, muscle, heart, kidney, brain and skin.

6. A process according to claim 3 wherein the ribosome preparation is prepared from plant cells.

7. A process according to claim 6 wherein the plant cells are from wheat germ.

8. A process according to claim 1 wherein the pH is below about 7.5.

9. A process according to claim 1 wherein the reaction mixture further comprises KCl.

10. A process according to claim 1 wherein the reaction mixture further comprises DTT and MgCl$_2$.

* * * * *

UNITED STATES PATENT AND TRADEMARK OFFICE
CERTIFICATE OF CORRECTION

PATENT NO. : 4,374,197
DATED : February 15, 1983
INVENTOR(S) : Bernard L. Horecker It is certified that error appears in the above-identified patent and that said Letters Patent is hereby corrected as shown below:

Column 1, line 33, "9498" should read: 94-98

Column 3, line 59, "23302334" should read: 2330-2334

Column 3, line 63, "3 mMg Cl$_2$" should read: 3 mM MgCl$_2$

Column 4, line 5, "1.5 MKCl" should read: 1.5M KCl

Column 4, line 22, "concentration" should read: concentrate

Column 4, line 30, "17" should read: 1-7

Column 5, line 55, "1.5 MKCl" should read: 1.5M KCl

Signed and Sealed this

Fifth Day of June 1984

[SEAL]

Attest:

GERALD J. MOSSINGHOFF

Attesting Officer     Commissioner of Patents and Trademarks